United States Patent [19]
Feldner et al.

[11] Patent Number: 4,758,352
[45] Date of Patent: Jul. 19, 1988

[54] PROCESS FOR THE TREATMENT OF HYDROLYSIS RESIDUES FROM ORGANO CHLOROSILANE SYNTHESIS

[75] Inventors: Kurt Feldner; Otto Horak, both of Cologne, Fed. Rep. of Germany

[73] Assignee: Bayer Aktiengesellschaft, Leverkusen, Fed. Rep. of Germany

[21] Appl. No.: 872,991

[22] Filed: Jun. 11, 1986

[30] Foreign Application Priority Data

Jul. 2, 1985 [DE] Fed. Rep. of Germany ....... 3523543

[51] Int. Cl.[4] ................................................ C02F 1/52
[52] U.S. Cl. .................................... 210/719; 210/758; 556/477
[58] Field of Search ............... 210/719, 737, 738, 758, 210/761, 762, 766, 912; 556/466, 472, 477

[56] References Cited

U.S. PATENT DOCUMENTS

| 2,380,995 | 8/1945 | Rochow | 556/472 |
| 4,174,280 | 11/1979 | Pradt et al. | 210/758 |
| 4,221,691 | 9/1980 | Danielson et al. | 528/12 |
| 4,244,818 | 1/1981 | Abson | 210/758 |

FOREIGN PATENT DOCUMENTS

| 0089784 | 9/1983 | European Pat. Off. . |
| 901889 | 5/1953 | Fed. Rep. of Germany . |
| 2362494 | 7/1975 | Fed. Rep. of Germany . |
| 3005743 | 8/1980 | Fed. Rep. of Germany . |

Primary Examiner—Peter Hruskoci
Attorney, Agent, or Firm—Sprung Horn Kramer & Woods

[57] ABSTRACT

A process is provided for the treatment of high-boiling, solids- and copper-containing residues produced during organochlorosilane synthesis. The process comprises hydrolyzing, oxidizing the hydrolyzed residues with a free oxygen-containing gas and separating-out a copper-containing solution.

13 Claims, 3 Drawing Sheets

PROCESS FOR THE TREATMENT OF HYDROLYSIS RESIDUES FROM ORGANO CHLOROSILANE SYNTHESIS

BACKGROUND OF THE INVENTION

This invention relates to a process for the working-up of hydrolysis residues which are produced during the hydrolysis of solids-containing polysilane sludges from organochlorosilane synthesis by the direct process. The present invention relates, in particular, to the working-up of hydrolysis residues from methyl chlorosilane synthesis.

Organochlorosilanes and, in particular, the methyl chlorosilanes serve as starting materials for the production of silicones which are widely used, for example, as rubbers, crack sealants, oils, building protecting agents etc. Dimethyl dichlorosilane, which is obtained in a high yield if the direct reaction of silicon with methyl chloride is catalyzed by copper or copper compounds, is particularly desirable during the production of methyl chlorosilanes. The process is basically described in U.S. Pat. No. 2,380,995. Methyl chlorosilanes are produced on an industrial scale world-wide by this process, the reaction normally being carried out in continuously operating fluidized bed reactors.

It is known that further silanes corresponding to the general formula $Me_xSiCl_{4-x}$, $x=0$ to 4, $Me_xHSiCl_{3-x}$, $x=0$ to 2, ($Me=CH_3-$) as well as dimeric silanes $Me_x-Si_2Cl_{6-x}$, $x=2$ to 6, siloxanes and silylmethylenes are formed during direct synthesis in addition to dimethyl dichlorosilane.

The finest contents of silicon, catalyst and reacted contact mass are carried off continuously together with the reaction product, the crude silane mixture, and unreacted methyl chloride, when carrying out the direct process in fluidized bed reactors. These dust contents are frequently collected together with the highest boiling reaction products ($Kp_{760} > 160°$ C.) in a so-called sludge vessel with an associated washing tower. The temperature of the vessel in which the conventional excess pressure of from 1.5 to 10 bar prevails is generally adjusted such that the mixture of solids and condensed fractions is kept sufficiently thinly liquid to allow discharge from this vessel.

According to German Patent No. 2,362,494, the content of the sludge vessel may be depressurized into a stirrerequipped container being under normal pressure and the still-distillable fractions may then be separated from the mixture by heating. The content of this vessel is then generally subjected to hydrolysis.

Actual hydrolysis may be carried out in a waste-pipe in the manner described in DE-PS No. 2,362,494. The disadvantage resides in the fact that hydrolysis is often incomplete owing to the short contact times and that large quantities of water are used.

DE-OS No. 3,005,743 describes a hydrolysis process in which the unpleasant property of adhesion of the hydrolysates is avoided by addition of mineral oil. However, since the hydrolysis are considered to be worthless and have to be dumped, the additional organic content is disadvantageous.

EP No. 0,089,784 teaches that the problem of adhesion may be overcome by observing a minimum chlorine content, but this object is difficult to achieve industrially.

In all the above-mentioned processes, a hydrochloric acid suspension is formed in which the fairly solid hydrolysate is considered to be worthless and has to be dumped. However, these hydrolysates are not without problems as they usually contain from 2 to 10% of predominantly metallic copper which may be partially eluted from the dumped hydrolysis and may therefore represent a pollution hazard for ground water. Furthermore, most hydrolysates obtained are sensitive to oxidation and, in some cases, they even have a tendency for self-ignition, and this prevents dumping according to environmental regulations.

Up to 100 g/l of HCl which are dissolved in the hydrolysis water are obtained by hydrolysis of the Si-Cl-functions. Furthermore, the hydrolysis suspensions which are not further treated may evolve hydrogen, and this is undesirable and may even be dangerous.

It is known from German Patent No. 901,889 that exhausted silicon- and copper-containing contact compositions obtained from the reactor during the production of organochlorosilane may be worked-up by treatment in water or dilute hydrochloride acid with gaseous chlorine. The unchanged elemental silicon is separated from the copper-containing solution after chlorination and the copper-II-chloride is converted into copper-I-chloride by reducing agents, is crystallized out and is re-used as catalyst in silane synthesis.

This process is unsuitable for the hydrolysates under consideration here for two reasons:

Owing to the polysilane content in the material discharged from the sludge vessel, the hydrolysis suspension contains considerable proportions of compounds which are capable of chlorination, and this may lead to waste water problems.

On the other hand, copper cannot be separated quantitatively by crystallization from copper-I-chloride and, furthermore, other metals which are not precipitable as sparingly soluble chloride obviously also remain in solution.

SUMMARY OF THE INVENTION

The present invention accordingly relates to a hydrolysis treatment which is as effective as possible and to the further working-up of these hydrolysates, during which a solid residue which may be dumped according to regulations is formed, the copper is recovered and a waste water which is free from heavy metal is obtained.

An object of the present invention is accordingly to provide a process for the working-up of high-boiling and solids-containing residues formed during organochlorosilane synthesis, which is characterised in that the residues are hydrolysed, subsequently oxidized with a free oxygen-containing gas and the copper-containing solutions are separated and worked-up.

BRIEF DESCRIPTION OF THE DRAWINGS

FIG. 1 is a diagrammatic flow diagram of a prior art process. The gaseous reaction products, unreacted methyl chloride and fines leaving the direct synthesis reactors (12) pass via (13) into the sludge vessel (14) in which the non-volatile constituents are collected and volatile constituents leave the vessel via (15) to enter the product distillation (16). By means of a time valve the non-volatile content of (14) is depressurized and passed via (17) into a thickening vessel (18) in order to recover volatile compounds under atmospheric pressure.

From the vessel (18) the sludge is sucked via (19) into a waste pipe (20) by water and passed to hydrolysis. The suspension from (20) via (21) is normally collected in a container (22) and dumped.

FIG. 2

Figure 1:
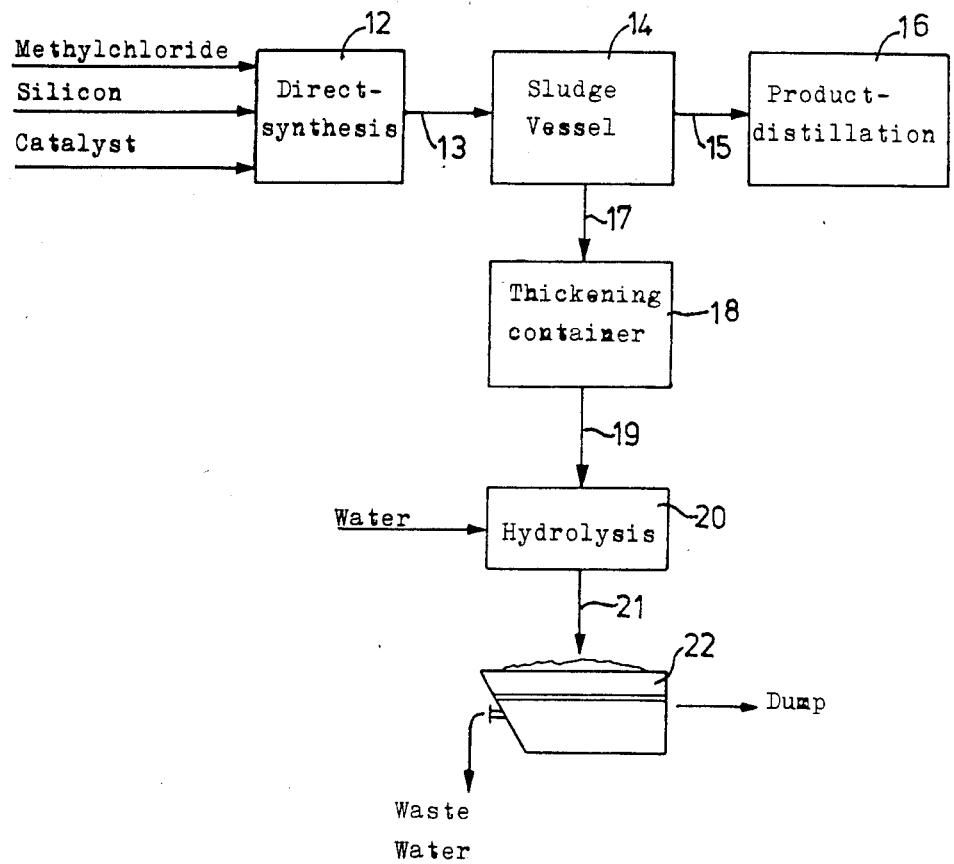
FIG. 1
Figure 2:
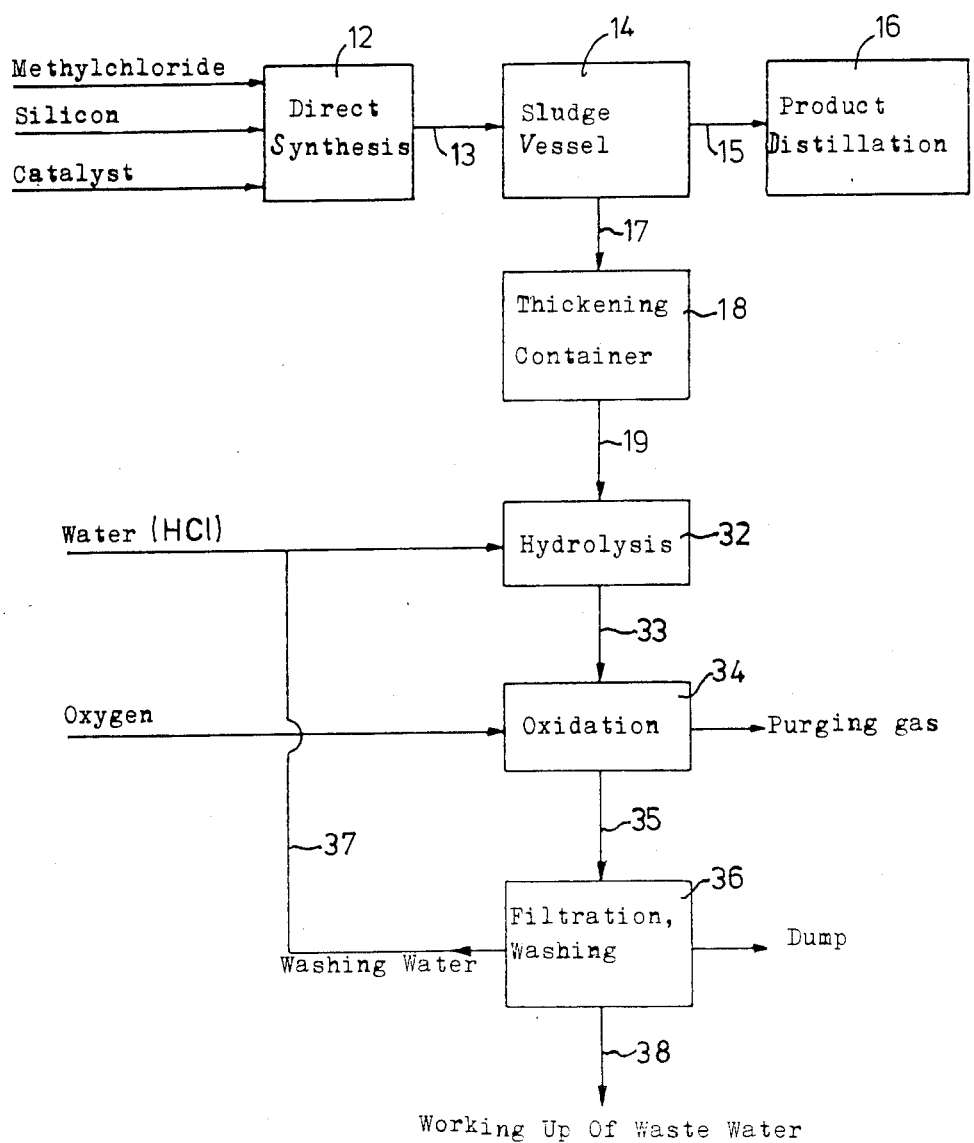

FIG. 2 is a diagrammatic flow diagram according to the present invention. The procedure of collecting the sludge is completely analogous to that described in FIG. 1 (step 12 to 19). The procedure then differs in that the hydrolysis is performed in a stirrer-equipped reaction vessel (32) with water or diluted HCl. The hydrolysis suspension passes via a free overflow (33) into the oxidation reactor (34). After oxidation is complete the suspension leaves the vessel (34) via (35) and is filtered using a suitable filtration device (36). After the separation of the solids from the liquid the washed solids are dumped, the copper-containing HCl solution is passed via (38) to the plant for working up the waste water (FIG. 3) and the washing water may be reused for hydrolysis, to which it is passed via (37).

FIG. 3

In the first step the copper-containing solution is adjusted to a pH value of 6 in the reduction vessel (39) using NaOH and simultaneously reduced using $SO_2$. The solution passes via line (40) into the precipitation vessel (41) in which copper (I) oxide is precipitated using NaOH. The resulting suspension is passed via (42) to a thickener (43), from the overflow of which solid-free effluent is passed to a clarification plant via line (46). The thickened suspension is passed via line (44) to a suitable filter (45) and filtered.

DETAILED DESCRIPTION OF THE INVENTION

The preferred hydrolysis method for the present invention involved carrying out hydrolysis using water or a highly diluted hydrochloride acid to about 5%, by weight in a stirrer-equipped reaction vessel with a fast-running disc stirrer, this container not being equipped with baffles so that a vortex may form, into which the material to be hydrolyzed is introduced. Hydrolysis is conducted at a temperature of 40° C. to 100° C. The preferred temperature is from 60° C. to 90° C. Finely divided, solid hydrolysates in which >90% of the particles have diameters <5 mm and which do not stick together are surprisingly obtained. The hydrolysis suspensions obtained normally have solids contents of from 5 to 40%, by weight, calculated as a moist filter cake, obviously depending on the quantities used.

Solids contents of from 20±5%, by weight, calculated as above, are optimal for further processing according to the present invention. However, this quantity does not represent a restriction for the present invention.

Oxidation of the hydrolysis suspension according to the present invention is advantageously carried out using gases containing elemental oxygen, preferably using commercially pure oxygen at a pressure above atmospheric pressure.

Oxidation according to the present invention is generally carried out at $O_2$ pressure of from 1 to 20 bar, preferably from 4 to 6 bar. The oxygen consumed during oxidation is continuously replaced in order to maintain the desired pressure. The temperature may vary from 50° C. to 120° C. and a temperature of 80° C.±10° C. has proven to be optimal. The residence time during oxidation is 1 to 5 hours and is generally three hours. Shorter residence times, lower pressures or temperatures are possible, but there is a risk of that the dried residue may no longer be thermally inert. There is no upper limit to the residence times, but residence times >4 hours are uneconomic and demand unnecessarily large reaction vessels. The process according to the present invention may be carried out batchwise, as well as continuously.

In contrast to the use of other oxidizing agents, such a NaOCl, chlorine or hydrogen peroxide, the contents of chlorinated hydrocarbons in the waste water are substantially lower after separating the solids. Oxygen pressure oxidation also has the advantage over oxidation using other oxidizing agents in that metering problems do not arise because an $O_2$ excess is quite uncritical and a deficit is impossible according to the present process. Neither the quantity of waste water nor the salt load is additionally increased during oxidation with oxygen.

After completion of oxidation, the $O_2$ pressure is released and solids are separated from the fluid.

As acidic hydrolysis of the Si-Si-bonds, which takes place with $H_2$ formation, cannot be suppressed completely relative to oxidation, i.e., a small amount of $H_2$ is evolved. To avoid an explosive atmosphere, a quantity of the gas volume in the reaction vessel is continuously exchanged by purging with $O_2$. The composition of the gaseous phase is controlled without difficulty in this manner.

In a preferred embodiment, the separation of the solids is carried at elevated temperature and the solids are freed from adhering copper-containing solution by washing and are cooled.

The solids are preferably separated by means of a filter device, for example, a belt-filter. A compact, thermally inert filter cake which is capable of being dumped, does not give off-gas and does not contain elutable heavy metals is obtained. The term "thermally inert" refers to a material which maintains a temperature of about 80° C. for two hours without spontaneous ignition. For this purpose, 5 g of the substance are poured into the open base (diameter 55 mm) of a Petri dish and maintained at 80° C. in a thermostatically controlled and stirred oil bath.

The solids content of the filter-cake is about 50%, by weight, (calculated as dry substance) and the copper content is <0.5%, by weight.

The majority of the copper contained in the sludge vessel discharge (from about 90 to 95%) is now in the filtrate which contains, in addition to from 10 to 80 g/l of HCl, from about 5 to 15 g/l of Cu and from 0.1 to 1.0 g/l of Fe, Zn, Al and $SiO_2$, respectively.

No more copper may be eluted with further water from the oxidized, separated and washed solid material, it evolves no further hydrogen and is still inert towards air at 80° C. after drying, allowing for unproblematical dumping.

The process for working-up the hydrolysates in accordance with the present invention involves oxidizing the hydrochloric acid hydrolysis suspensions as desired and reacting the copper, iron, aluminum and zinc-containing solutions, optionally with addition of reducing agents, with alkaline earth and/or alkali metal hydroxide, after separating the solids. A waste water which (a) is almost neutral and (b) is free from heavy metals which may be precipitated as hydroxides, is obtained in this way after separating the precipitated hydroxides and oxides.

A preferred method of separating the filtrate form the dissolved metal salts involves reducing precipitation with $SO_2$ and NaOH. The reduction being carried out in a first stage at a pH of about 6 and precipitation being completed in a second stage at pH 9. The reducing precipitation is preferably carried out with heating at from about 50° C. to 100° C. It is beneficial during filtrating of the oxidized hydrolysis suspension to feed the hot copper-containing filtrate directly to the copper recovery treatment and to recirculate the colder, less markedly contaminated washing water into the hydrolysis treatment.

A readily filterable copper(I) oxide is obtained, which has a copper content of from 40 to 60%, as well as also precipitated oxides and hydroxides of iron, zinc, aluminium and silicon in quantities of from 1 to 5%, respectively, after drying.

Waste water is freed from heavy metals in this way and may optionally be supplied to a biological clarification plant for further cleaning.

The present invention will be described in more detail below with reference to the following non-limiting

EXAMPLES.

EXAMPLE 1

From about 300 to 400 kg of non-volatile constituents from a stirrer-equipped container for the recovery of volatile silanes at normal pressure were supplied hourly via a time valve to an hydrolysis treatment. The hydrolysis container was in the form of a stirrer-equipped vessel with rapidly running disc mixer without baffles. Simultaneously with the silane residues to be hydrolysed, the vessel was charged with water which has been pre-heated such that a hydrolysis temperature of from 70° C. to 80° C. was adjusted. The average residence time was about 0.5 hours and the hydrolysis suspension left the vessel as a free overflow.

A solid, crumbly hydrolysate was generally obtained. The following characteristics were typical of such hydrolysates:

| | |
|---|---|
| Solids content: | from 5 to 20%, by weight, dry substance |
| Particle distribution of the solids: | 95% < 5 mm, 50% < 1 mm, 10% < 0.1 mm |
| Cu content in the dry solids: | from 5 to 9%, by weight |
| hydrolysis water: | from 20 to 100 g/l HCl from 50 to 200 ppm $Cu^{2+}$ |
| Oxidation sensitivity of the dry hydrolysate: | spontaneous ignition at 80° C. after 0 to 5 minutes. |

EXAMPLE 2

12 liters of the hydrolysis suspension from the hydrolysis apparatus described in Example 1 were oxidized without further pretreatment. An enamelled autoclave having a volume of 16 liters and equipped with a self-sucking hollow stirrer and temperature measuring means was used as reaction vessel. The autoclave was charged with 6 bar of $O_2$ from a steel cylinder. About 30 l/h of $O_2$ were purged through the autoclave continuously to allow the composition of the gaseous phase to be controlled and to maintain the $H_2$ concentration below 2%, by volume. The starting temperature during oxidation was 51° C. The temperature rose to 69° C. due to the initiating exothermic oxidation. The temperature was maintained at 80° C. by steam heating during the further three hours oxidation time.

| Starting Suspension: | |
|---|---|
| Solids content of the suspension (dry): | 14.8% |
| Cu content of the solids (dry): | 5.6% |
| Oxidation sensitivity of the dry-hydrolysate at 80° C. in air: | Spontaneous ignition after less than 1 minute |
| HCl content of the water: | 54.5 g/l |
| After oxidation: | |
| Cu Content of the dry solids: | 0.28% |
| Oxidation sensitivity of the dry solids at 80° C. in air: | inert |
| HCl content of the water: | 47.8 g/l |
| $Cu^{2+}$ content of the water: | 8.0 g/l |
| $O_2$ consumption: | 10 l/l suspension. |

EXAMPLE 3

70 l of the $CuCl_2$-containing solutions containing 7.4 g Cu/l and contained from several batches according to Example 2 were heated to 70° C. in a 100 l glass stirrerequipped vessel and adjusted to pH 6 using about 17 l of 15% strength sodium hydroxide solution. Then 105 l of gaseous $SO_2$ were introduced (about 3.5 l $SO_3$/min) over a period of 30 minutes whilst stirring (150 u.p.m.); during this time the mixture was further kept at a constant pH of 6 by slowly adding 15% strength sodium hydroxide solution. After the $SO_2$-introduction was complete the reaction mixture was adjusted to pH 8.9-9 over a period of about 15 minutes using 15% strength NaOH and then the suspension was stirred for a further hour. Following the precipitation the mixture was filtered in a chamber filter press using an excess pressure of up to a maximum of 6 bars until the dehydration was completed after that the filter cake was washed. The residue was dried at 120° C. to constant weight in a vacuum drying over; the dry residue was light orange in colour and contained 52.4% of copper. The ignition los (1 h at 400° C.) was about 8-10%. The filtrate of the filter cake was free of heavy metals (<50 mg/l).

It will be appreciated that the instant specification and claims are set forth by way of illustration and not limitation, and that various modifications and changes may be made without departing from the spirit and scope of the present invention.

What is claimed is:

1. A process for the treatment of high-boiling solids- and copper-containing residues produced during organochlorosilane synthesis, comprising (a) hydrolyzing the residues, (b) oxidizing the hydrolyzed residues from step (a) using oxygen in a free oxygen-containing gas and separating out copper-containing solutions from said hydrolyzed oxidized residues from step (b), wherein the oxidizing is conducted from 1 to 5 hours at a temperature of 50° C. to 120° C. and at a pressure of 1 to 20 bar.

2. A process according to claim 1, wherein the hydrolysis is carried out at from 40° C. to 100° C.

3. A process according to claim 1, wherein the hydrolysis is conducted in a stirrer-equipped container in which a vortex is produced by a rapidly running disc mixer.

4. A process according to claim 1, wherein the hydrolysis is conducted at a temperature of 60° C. to 90° C.

5. A process according to claim 1, wherein the hydrolysis is conducted with water.

6. A process according to claim 1, wherein the hydrolysis is conducted with highly diluted hydrochloric acid.

7. A process according to claim 1, wherein the oxidation is conducted at a pressure of 4 to 6 bars.

8. A process according to claim 1, wherein the oxidation is conducted at a temperature in the range of 80° C.±10° C.

9. A process according to claim 1, wherein the oxidation is conducted using pure oxygen.

10. A process according to claim 1, which further comprises conducting the oxidizing in an oxidative reaction vessel containing a gas volume and exchanging a portion of the gas volume in said vessel by continuously conducting purging with oxygen so as to avoid an explosive atmosphere in the vessel.

11. A process according to claim 1, wherein copper is recovered from said copper-containing solutions using reducing precipitation with heating at 50° C. to 100° C.

12. A process according to claim 1, wherein the hydrolyzed residues contain 5 to 9 weight % copper.

13. A process according to claim 1, wherein the hydrolyzed residues contain 5 to 20 weight % solids on a dry basis.

* * * * *

UNITED STATES PATENT AND TRADEMARK OFFICE
CERTIFICATE OF CORRECTION

Figure 3:
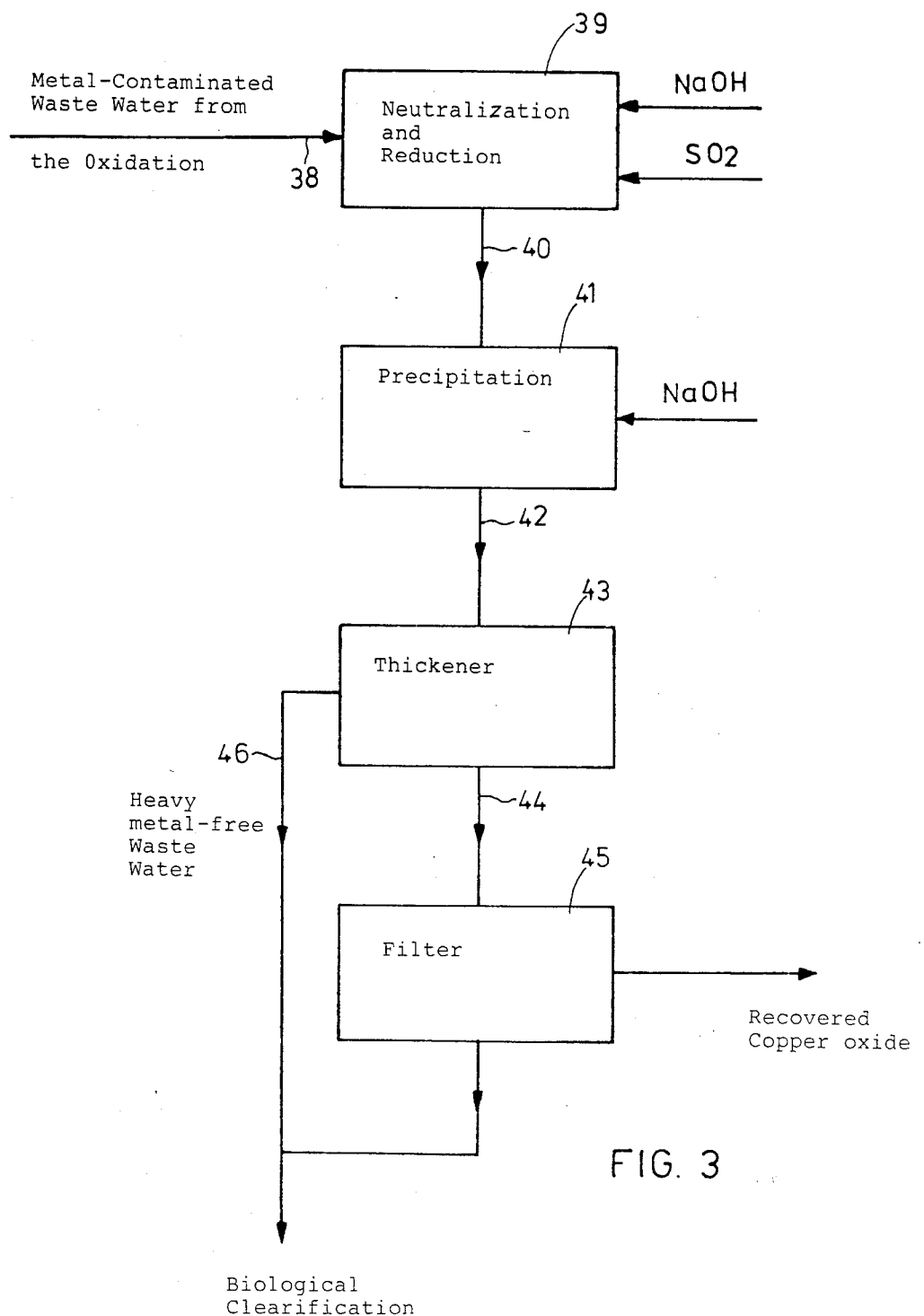

PATENT NO. : 4,758,352
DATED     : July 19, 1988
INVENTOR(S) : Kurt Feldner, et al It is certified that error appears in the above-identified patent and that said Letters Patent is hereby corrected as shown below:

| | |
|---|---|
| FIG. 3 | Bottom - correct spelling of --Clarification-- |
| Col. 1, line 60 | Delete "hydrolysis" and substitute --hydrolysates-- |
| Col. 2, line 5 | Delete "hydrolysis" and substitute --hydrolysate-- |
| Col. 3, line 38 | Delete "involved" and substitute --involves-- |
| Col. 4, line 11 | Before "NaOCl" delete "a" and substitute --as-- |
| Col. 5, line 3 | Delete "form" and substitute --from-- |
| Col. 5, line 24 | After "non-limiting" insert --Examples.-- |
| Col. 5, line 25 | Delete "EXAMPLES." |
| Col. 6, line 45 | Delete "over" and substitute --oven-- |
| Col. 6, line 62 | Delete "from" and substitute --for-- |

Signed and Sealed this

Thirty-first Day of January, 1989

Attest:

DONALD J. QUIGG

*Attesting Officer*      *Commissioner of Patents and Trademarks*